United States Patent
Alshemari

(10) Patent No.: US 8,626,309 B1
(45) Date of Patent: Jan. 7, 2014

(54) CONVEX CUP INTERNAL RECEIVER UNIT FOR A COCHLEAR IMPLANT

(71) Applicant: Hasan M. Sh. Sh. Alshemari, Saad Al-Abdulla (KW)

(72) Inventor: Hasan M. Sh. Sh. Alshemari, Saad Al-Abdulla (KW)

(*) Notice: Subject to any disclaimer, the term of this patent is extended or adjusted under 35 U.S.C. 154(b) by 0 days.

(21) Appl. No.: 13/892,192

(22) Filed: May 10, 2013

(51) Int. Cl.
*A61N 1/36* (2006.01)
(52) U.S. Cl.
USPC ............................................. 607/57
(58) Field of Classification Search
USPC .................... 607/136–137, 55–56
See application file for complete search history.

(56) References Cited

U.S. PATENT DOCUMENTS

| 4,532,930 | A | 8/1985 | Crosby et al. |
| 8,244,366 | B2 | 8/2012 | Chang et al. |
| 2002/0029074 | A1 | 3/2002 | Treaba et al. |
| 2004/0260361 | A1* | 12/2004 | Gibson ........................... 607/57 |
| 2008/0312717 | A1 | 12/2008 | Gantz |
| 2010/0160892 | A1* | 6/2010 | Tice .............................. 604/500 |

FOREIGN PATENT DOCUMENTS

EP 1951175 B1 11/2001

\* cited by examiner

*Primary Examiner* — Carl H Layno
*Assistant Examiner* — Paula J Stice
(74) *Attorney, Agent, or Firm* — Richard C. Litman

(57) ABSTRACT

The implantable medical device is configured as a cochlear implant or the like. The implantable medical device includes a stimulator unit, an elongate electrode carrier in electrical communication with said stimulator unit, and an internal receiver unit. The internal receiver unit is configured as a suction cup having first and second convex cup portions. The first convex cup portion is adapted for mounting against a bone surface. Preferably, each of the first and second convex cup portions is formed from a resilient, flexible, biocompatible material. The second convex cup portion has a central bore formed therein. When the second convex cup portion is mated against the first convex cup portion, a threaded screw extends through the bore to contact the first convex cup portion and is tightened, thus compressing the first convex cup portion against the bone surface for suctional adhesion thereto.

4 Claims, 4 Drawing Sheets

CONVEX CUP INTERNAL RECEIVER UNIT FOR A COCHLEAR IMPLANT

BACKGROUND OF THE INVENTION

1. Field of the Invention

The present invention relates to implantable medical devices, and particularly to cochlear implants or the like utilizing a suction cup for securement against a bone surface.

2. Description of the Related Art

A cochlear implant is a surgically implanted electronic device that provides a sense of sound to a person who is profoundly deaf or severely hard of hearing. Cochlear implants may help provide hearing in patients who are deaf due to damage to sensory hair cells in their cochleas. In these patients, the implants often can enable sufficient hearing for better understanding of speech. The quality of sound is different from natural hearing, with less sound information being received and processed by the brain. However, many patients are able to hear and understand speech and environmental sounds. Cochlear implants are well known in the field of implantable medical devices. One such implant is shown in U.S. Pat. No. 4,532,930, which is hereby incorporated by reference in its entirety.

Cochlear implant systems typically consist of two components, namely, an external component, commonly referred to as a processor unit, and an internal, implanted component, commonly referred to as a receiver/stimulator unit. The internal component is implanted in the patient's skull, under the skin. In order to fix the internal component to the patient's skull, typical conventional cochlear implantation utilizes drilling into the patient's cortical bone to form anchor holes, and the internal component unit is then secured to the skull using bone screws or the like. Given the high risks involved in invasive surgical procedures, particularly in drilling into a patient's skull, it would be highly desirable to provide a far less invasive method of securing a cochlear implant to a patient's cortical bone.

Thus, an implantable medical device solving the aforementioned problems is desired.

SUMMARY OF THE INVENTION

The implantable medical device is configured as a cochlear implant or the like. The implantable medical device includes a stimulator unit, an elongate electrode carrier in electrical communication with the stimulator unit, and an internal receiver unit. The internal receiver unit is configured as a suction cup having first and second convex cup portions. The first convex cup portion is adapted for mounting against a bone surface. Preferably, each of the first and second convex cup portions is formed from a resilient, flexible, biocompatible material.

Preferably, the second convex cup portion has a central aperture formed therethrough. When the second convex cup portion is mated against the first convex cup portion, a threaded screw, which passes through the aperture to contact the first convex cup portion, is tightened, thus compressing the first convex cup portion against the bone surface for suctional adhesion thereto.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
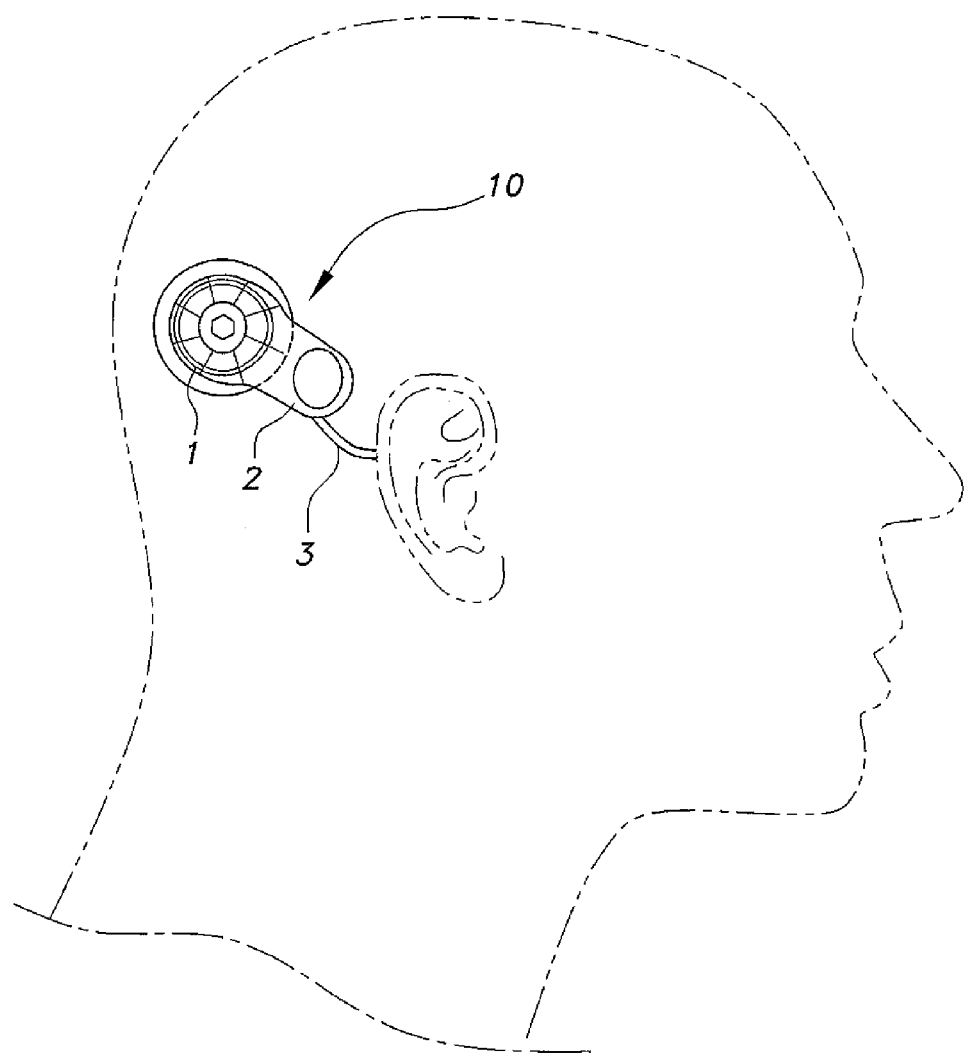
FIG. 1 diagrammatically illustrates implantation of an implantable medical device according to the present invention against a patient's cortical bone.

FIG. 1 illustrates the implantable medical device 10 implanted within the head of a patient, fixed adjacent the patient's cortical bone. As shown, the implantable medical device 10 may be configured as a cochlear implant, although it should be understood that the implantable medical device 10 may be configured as any suitable type of medical implant or the like. As shown, device 10 includes an internal receiver unit 1, a stimulator unit 2, and an elongate electrode carrier 3, as are well known in the field of cochlear implants and the like. As is also well known in the field of implantable medical devices, the internal receiver unit 1, stimulator unit 2 and elongate electrode carrier 3 are preferably hermetically sealed within a biocompatible housing formed from silicone or the like.

Figure 2:
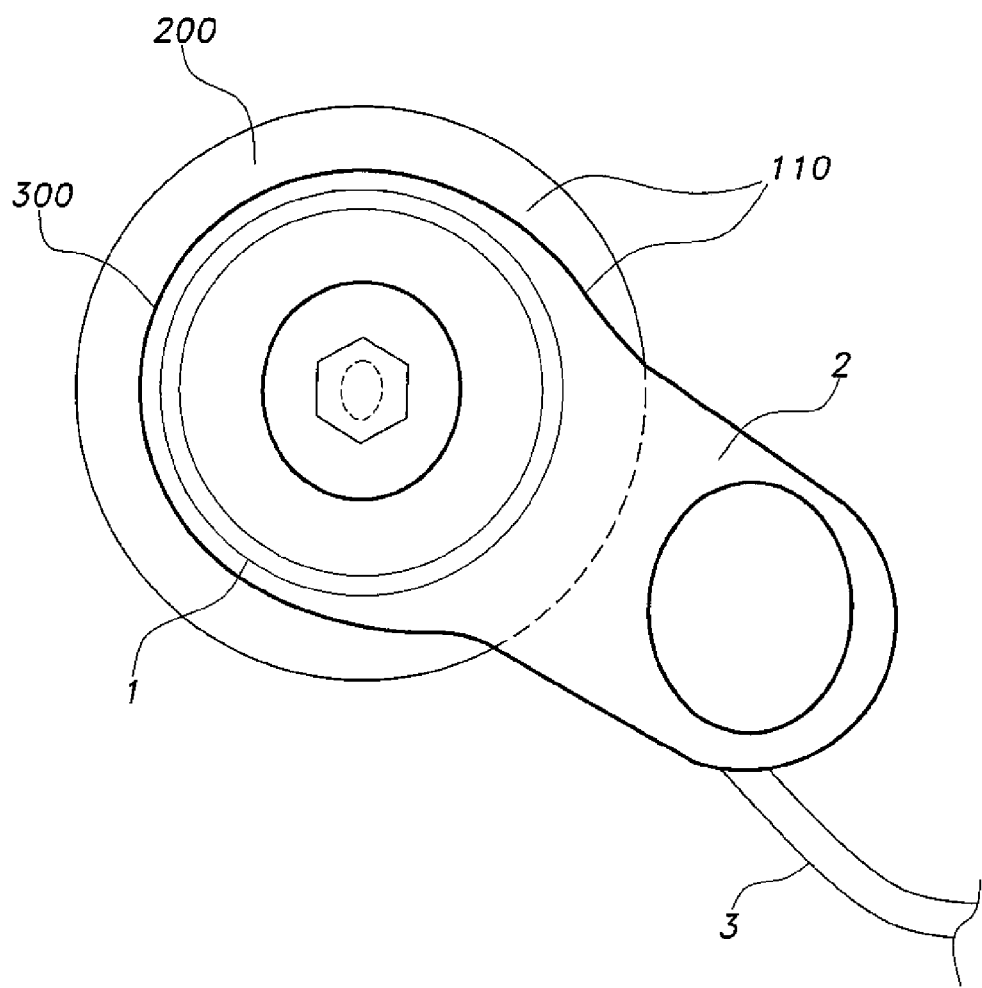
FIG. 2 is a plan view of the implantable medical device according to the present invention.
Figure 3:
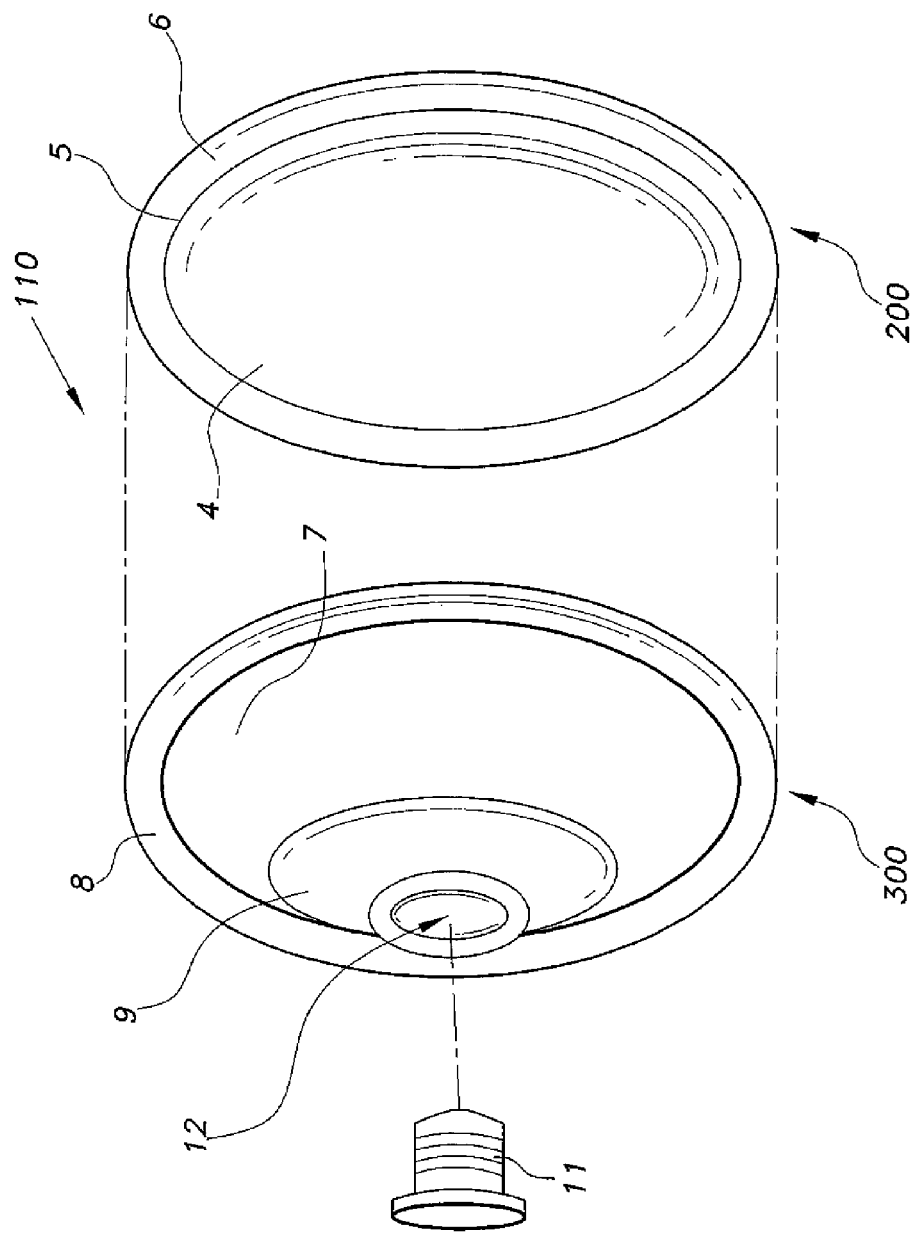
FIG. 3 is an exploded, perspective view of a suction cup assembly of the implantable medical device of FIG. 1.

As best shown in FIGS. 2 and 3, the internal receiver unit 1 unit is configured as a suction cup for mounting on the patient's cortical bone. The overall suction cup assembly 110 includes a first convex cup portion or layer 200, having a central convex suction pad 4. The central convex suction pad 4 is defined by a substantially circular, peripheral edge 5, from which extends a flat, annular flange 6. The flat, annular flange 6 extends about the peripheral edge 5 and is preferably formed from a biocompatible, resilient material.

Figure 4:
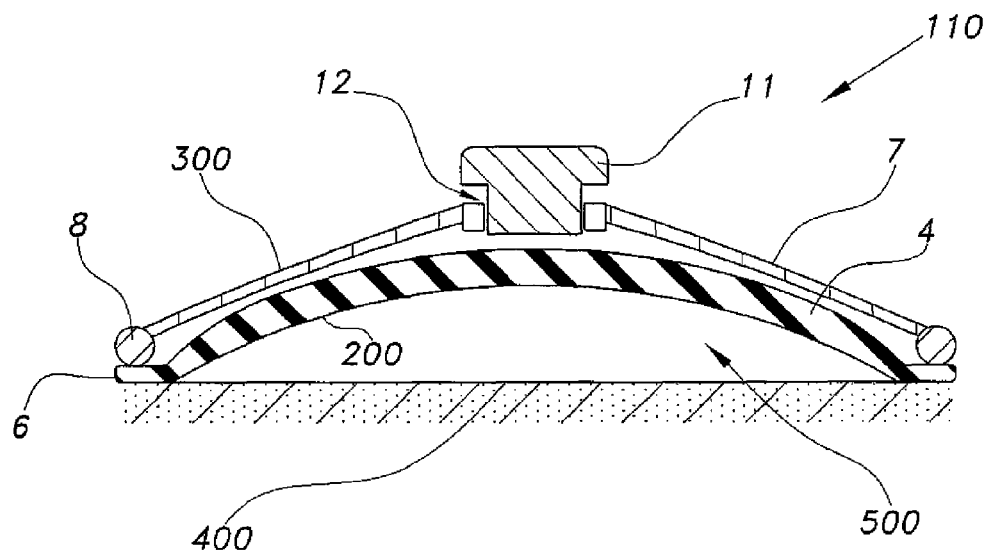
FIG. 4 is a side view in section of the suction cup assembly of FIG. 3, illustrated in a non-compressed state.

A second convex cup portion or layer 300 mates with, and is mounted over, the convex face of the suction pad 4. The second convex cup portion includes a convex frame 7 having an annular, outer pressing portion 8 peripherally extending therefrom. Pressing portion 8 is also preferably formed from a biocompatible, resilient material. The second convex cup portion 300 also includes a central, ring-shaped fastening portion 9 having a bore 12 formed centrally therethrough. The pressing portion 8 is mated against the flat flange 6 of suction pad 4, as best seen in FIG. 4. A central screw 11 is threaded into the bore 12 of the central, ring-shaped fastening portion 9. Preferably, both the central screw 11 and the central, ring-shaped fastening portion 9 are formed from a biocompatible material, such as titanium. The central, ring-shaped fastening portion 9, the central screw 11, or both are magnetic, thus forming the magnet of the cochlear implant, as is well known in the field of cochlear implants. The antenna of the cochlear implant, as is well known in the field of cochlear implants and the like, is preferably mounted within the pressing portion 8.

Figure 5:
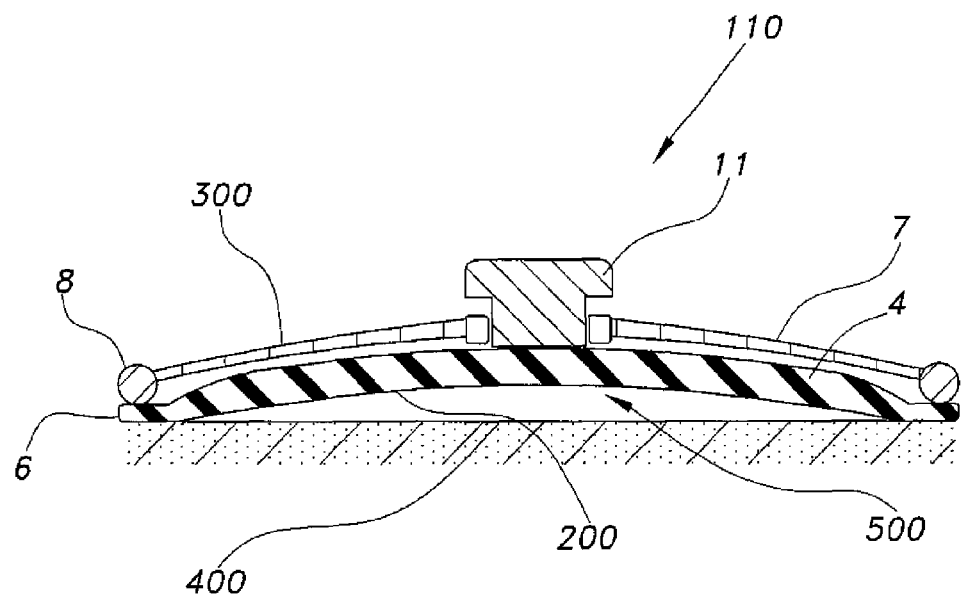
FIG. 5 is a side view in section of the suction cup assembly of FIG. 3, illustrated in a compressed state.

As shown in FIG. 5, after placing the central screw 11 in the bore 12 of the central, ring-shaped fastening portion 9, the center of the suction cup assembly 110, including the suction pad 4, is pressed against the outer surface 400 of a bone, such as the cortical bone. The open volume 500 defined by the concave, lower portion of the first cup portion 200 is reduced as the central screw 11 pushes the suction pad 4 against the bone surface 400. This action causes any air or other fluid within volume 500, between the suction pad 4 and the bone outer surface 400, to be expelled past the rims 6 and 8.

Preferably, the suction cup assembly 110 is formed from a generally elastic and resilient material. Thus, when the user ceases to apply pressure to the center of the outside of the suction cup assembly 110 (via central screw 11), the suction cup assembly 110 is generally restored to its original, curved shape. The decrease in volume of space 500 also results in a decrease in fluid pressure, creating a pressure differential, similar to a conventional suction cup, which fixes the internal components of cochlear implant 10 to the bone outer surface 400.

Although the implantable medical device 10 is shown as having only a single suction cup attachment, it should be understood that any desired number of suction cup attachments may be utilized. Further, although shown as having the internal receiver unit 1 configured as a suction cup, it should be understood that any suitable portion of the implant may be configured as a suction cup. Additionally, it should be further understood that the first convex cup portion 200 may be configured having additional features or layers that are common to suction cups, such as additional gel layers, semi-gel layers or the like. The first convex cup portion 200 is preferably formed from a silicone rubber or other elastomeric biocompatible material having a relatively high coefficient of friction with respect to the bone surface 400.

It is to be understood that the present invention is not limited to the embodiments described above, but encompasses any and all embodiments within the scope of the following claims.

I claim:

1. An implantable medical device, comprising:
   a stimulator unit;
   an elongate electrode carrier in electrical communication with the stimulator unit; and
   an internal receiver unit, the internal receiver unit having a substantially convex contour defining a suction cup for attachment to a bone surface, the internal receiver unit comprises first and second convex cup portions, the first convex cup portion being adapted for mounting against the bone surface and including:
   i) a central convex suction pad having a substantially circular peripheral edge; and
   ii) a flat, annular flange extending from the substantially circular peripheral edge of the central convex suction pad;
   the second convex cup portion comprises:
   i) a convex frame portion having a substantially circular peripheral edge;
   ii) an outer peripheral portion annularly formed on the substantially circular peripheral edge of the convex frame portion; and
   iii) a central, ring-shaped fastening portion and a central bore extending through the central, ring-shaped fastening portion.

2. The implantable medical device as recited in claim 1, further comprising a threaded screw threadable into the bore, whereby when said first and second convex cup portions are mated together, axial movement of the threaded screw selectively presses a central portion of the first convex cup portion against the bone surface for suctional attachment thereto.

3. The implantable medical device as recited in claim 2, wherein said first and second convex cup portions are each formed from a resilient, flexible, biocompatible material.

4. A method of securing an implantable medical device to a bone surface, comprising the steps of:
   providing an implantable medical device having an internal receiver unit having a substantially convex body defining a suction cup, wherein the body of the internal receiver unit has first and second convex cup portions; and
   securing the implantable medical device to a bone surface through suction between the suction cup and the bone surface, wherein the step of securing the implantable medical device to the bone surface comprises:
   i) pressing against a central portion of the first convex cup portion to generate the suction against the bone surface; and
   ii) tightening a threaded screw through a bore formed through the second convex cup portion and contacting the first convex cup portion.

* * * * *